(12) United States Patent
Shuguang et al.

(10) Patent No.: US 6,723,862 B2
(45) Date of Patent: Apr. 20, 2004

(54) FATTY ACID ISOMERIZATION WITH MESOPOROUS ZEOLITES

(75) Inventors: Zhang Shuguang, New Rochelle, NY (US); Zhang Zongchao, Norwood, NJ (US)

(73) Assignee: Akzo Nobel N.V. (NL)

( * ) Notice: Subject to any disclaimer, the term of this patent is extended or adjusted under 35 U.S.C. 154(b) by 0 days.

(21) Appl. No.: 10/390,851

(22) Filed: Mar. 18, 2003

(65) Prior Publication Data

US 2003/0191331 A1 Oct. 9, 2003

Related U.S. Application Data

(60) Provisional application No. 60/369,415, filed on Apr. 2, 2002, and provisional application No. 60/438,975, filed on Jan. 9, 2003.

(51) Int. Cl.$^7$ ............................................. C07C 51/353
(52) U.S. Cl. ...................... 554/125; 423/277; 423/718; 502/77
(58) Field of Search .................. 554/125; 423/277, 423/718; 502/77

(56) References Cited

U.S. PATENT DOCUMENTS

| | | | |
|---|---|---|---|
| 4,831,006 A | 5/1989 | Aufdembrink | 502/242 |
| 5,057,296 A | 10/1991 | Beck | 423/277 |
| 5,198,203 A | 3/1993 | Kresge et al. | 423/718 |
| 5,686,935 A | 11/1997 | Weisbrod | 345/100 |

FOREIGN PATENT DOCUMENTS

| | | | |
|---|---|---|---|
| CN | 01135624.3 | 11/1996 | |
| EP | 0683150 A1 | 11/1995 | .......... C07C/51/353 |
| EP | 0774451 A1 | 5/1997 | .......... C07C/51/353 |
| WO | WO 01/66507 A2 | 9/2001 | .......... C07C/51/353 |
| WO | WO 03/006157 A2 | 1/2003 | ............ B01J/29/06 |

OTHER PUBLICATIONS

Chemical Materials, 2002, 14, 1144), Hydrothermally Stable Ordered Hexagonal Mesoporous Aluminosilictes Assembled from a Triblock Copolymer and Performed Aluminosilicate Precursors in Strongly Acidic Media, Yu Han, et al.

Angew. Chem. Int. Ed. 2001, 40, No. 7, Steam–Stable MSU–S aluminosilicate Mesostructures Assembled from Zeolite ZSM–5 and Zeolite Beta Seeds, pp. 1255–1258.

Angew. Chem. Int. Ed. 2001, 40, No. 7, Strongly Acidic and High–Temperature Hydrothermally Stable Mesoporous Aluminosiicates with Ordered Hexagonal Structure, Zongtao Zhang, et al, pp. 1258–1262.

J. Am. Chem.. Soc., 2001, 123, Mesoporous Aluminosilicates with Ordered Hexagonal Structure Strong Acidity, and Extraordinary Hydrothermal Stability at High Temperatures, Zongtao Zhang, et al, pp. 5014–5021.

J. Am. Chem. Soc. 2000, 122, Steam–Stable Alumnosilicate Mesostructures Assembled from Zeolite tuype Y Seeds, Yu Liu, et al., pp. 8791–8792.

J. Phys. Chem. B 2001, 105, A Novel Method for Incorporation of Heteroatoms into the Framework of Ordered Mesoporous Silica Materials Synthesized in Strong Acidic Media, Yu Han, et al, pp. 7963–7966.

International Search Report, No.: PCT/EP 03/03194, Aug. 14, 2003 (International Search Report, No.: PCT/EP 03/03194, Aug. 14, 2003).

*Primary Examiner*—Deborah D. Carr
(74) *Attorney, Agent, or Firm*—Ralph J. Mancini

(57) ABSTRACT

The present invention generally relates to a process for the preparation of branched fatty acids from straight chain unsaturated fatty acid feedstocks with a strongly acidic and hydrothermally stable mesoporous aluminosilicate and/or aluminophosphate catalyst materials having mesopores of 15–500 Å and contain primary and secondary nanosized zeolite structural units in the walls that separate mesopores.

33 Claims, No Drawings

FATTY ACID ISOMERIZATION WITH MESOPOROUS ZEOLITES

The present application claims priority of U.S. Provisional Patent Application Ser. Nos. 60/369,415, filed on Apr. 2, 2002 and 60/438,975, filed on Jan. 9, 2003.

FIELD OF THE INVENTION

The present invention generally relates to the isomerization of fatty acids with a strongly acidic and hydrothermally stable mesoporous aluminosilicate catalyst.

BACKGROUND OF THE INVENTION

Fatty acids are the building blocks for various compositions ranging from lubricants, polymers, solvents, cosmetics and the like. Fatty acids are generally obtained by hydrolysis of triglycerides of vegetable or animal origin. Naturally occurring triglycerides are esters of glycerol and generally straight chain, even numbered carboxylic acids, in size ranging from 10–24 carbon atoms. Most common are fatty acids having 12, 14, 16 or 18 carbon atoms. The fatty acids are either saturated or contain one or more unsaturated bonds.

Long, straight chain saturated fatty acids (C10:0 and higher) are solid at room temperature, which makes them difficult to process in a number of applications. Unsaturated long chain fatty acids, however, e.g. oleic acid are liquid at room temperature, so are easy to process, but are unstable because of the existence of double bond(s). Branched fatty acids mimic the properties of the straight chain unsaturated fatty acids in many respects, but do not have the disadvantage of being unstable. "Branched fatty acids" means fatty acids containing one or more alkyl side groups which are attached to the carbon chain backbone at any position. Therefore, branched fatty acids are for many applications more desirable than straight chain fatty acids. Commercial branched acids are not, however, naturally occurring materials.

Currently, branched fatty acids are obtained by isomerization (branching) of the straight chain, unsaturated fatty acids having a corresponding chain length. For example, branched C18:0 is prepared from straight C18:1 (or also C18:2). Various routes are known for said isomerization or branching of fatty acids in the art.

Porous inorganic solids have found great utility as catalysts and separations media for various industrial applications. The openness of their microstructure allows molecules to access the relatively large surface areas of these materials that enhance their catalytic and sorptive activity. Three broad categories of microporous materials are in use today. These categories, which employ details of their microstructure as a basis for classification, are the i) amorphous and paracrystalline solids, ii) the crystalline molecular sieves and iii) layered materials. The detailed differences in the microstructures of these materials manifest themselves as important differences in the catalytic and sorptive behavior of the materials, as well as in differences in properties used to characterize them, such as their surface area, composition, acidity, basicity, the sizes of pores and the variability in those sizes, the presence or absence of X-ray diffraction patterns and the details in such patterns, and the appearance of the materials when their microstructure is studied by transmission electron microscopy, infrared absorption, electron diffraction methods.

Amorphous and paracrystalline materials represent an important class of porous inorganic solids that have been used for many years in industrial applications. Typical examples of these materials are the amorphous silicas commonly used in catalyst formulations and the paracrystalline transitional aluminas used as solid acid catalysts and petroleum reforming catalyst supports. The term "amorphous" is used here to indicate a material with no long range order and can be somewhat misleading, since almost all materials are ordered to some degree, at least on the local scale. An alternate term that has been used to describe these materials is "X-ray indifferent".

Paracrystalline materials such as the transitional aluminas also have a wide distribution of pore sizes, but better defined X-ray diffraction patterns usually consisting of a few broad peaks. The microstructure of these materials consists of tiny crystalline regions of condensed alumina phases and the porosity of the materials results from irregular voids between these regions. Since, in the case of either material, there is no long range order controlling the sizes of pores in the material, the variability in pore size is typicaly quite high. The sizes of pores in these materials fall into a regime called the mesoporous range, which is generally in the range of from about 13 to 200 Angstroms.

In sharp contrast to these structurally ill-defined solids are materials whose pore size distribution is very narrow because it is controlled by the precisely repeating crystalline nature of the materials' microstructure. These materials are called "molecular sieves", the most important examples of which are zeolites. The pore/channel openings of typical zeolites ranges from 3–7.5 angstroms, although larger sizes have been reported.

Finally, layered materials contain layers capable of being spaced apart with a swelling agent, and may be pillared to provide materials having a large degree of porosity. Examples of such layered materials include clays. Such clays may be swollen with water, whereby the layers of the clay are spaced apart by water molecules. Other layered materials are not swellable with water, but may be swollen with certain organic swelling agents such as amines and quaternary ammonium compounds. Examples of such non-water swellable, layered materials include, but are not limited to, layered silicates, magadiite, kenyaite, trititanates and perovskites. Another example of a non-water swellable layered material, which can be swollen with certain organic swelling agents, is a vacancy-containing titanometallate material, as described in U.S. Pat. No. 4,831,006. Once a layered material is swollen, the material may be pillared by interposing a thermally stable substance, such as silica, between the spaced apart layers. Various pillaring materials and methods for pillaring water swellable and non-water swellable layered materials described therein and are known in the art.

Each of these materials does, however, have its limitations. Despite encouraging progress in recent years concerning amorphous and paracrystalline materials, both the acidity and hydrothermal stability at higher temperatures of the current materials are generally lower than those of microporous aluminosilicate zeolites. Crystalline microporous zeolites are very stable, can be made to have strong acidity, and are widely used commercially. However, their applications are limited due to their relatively small channel diameter. Finally, clay catalyzed isomerization suffers from two main disadvantages. First, a considerable amount of undesired side products containing oligomers, saturated straight chain fatty acids and intermediate dimers is formed. A second disadvantage is that the clay catalyst cannot be reused. Accordingly, processes which employ these materials for the preparation of branched fatty acids from straight chain unsaturated fatty acid feedstocks are typically plagued by low yield, undesireable byproduct formation and premature catalyst deactivation.

The present invention has solved many of the problems of the prior art by utilizing a catalyst having the positive attributes of both mesoporous and microporous type catalytic materials.

SUMMARY OF THE INVENTION

The present invention generally relates to a process for the preparation of branched fatty acids from straight chain unsaturated fatty acid feedstocks with a strongly acidic and hydrothermally stable mesoporous aluminosilicate and aluminophosphate catalyst materials having mesopores of 15–500 Å and contain primary and secondary nanosized zeolite structural units in the walls that separate mesopores.

DETAILED DESCRIPTION OF THE PRESENT INVENTION

The present invention generally relates to a process for the preparation of branched fatty acids from straight chain unsaturated fatty acid feedstocks with a strongly acidic and hydrothermally stable mesoporous aluminosilicate and aluminophosphate catalyst materials having mesopores of 15–500 Å and contain primary and secondary nanosized zeolite structural units in the walls that separate mesopores.

In one embodiment, the invention utilizes mesoporous aluminosilicates. However, other mesoporous materials based on other materials such as those comprising transition metals and post transition metals can also be employed. Catalytic materials such as those employable in the context of the present invention are described in Angewandte Chemie Int. Ed. (7, 2001, 1258), J. Am. Chem. Soc. (123, 2001, 5014), J. Phys. Chem. (105, 2001, 7963), J. Am. Chem. Soc. (122, 2000, 8791), Angew. Chem. Int. Ed. (40, 2001, 1255), and Chem. Mater. (14, 2002, 1144) and in Chinese Patent Application No. 01135624.3, which are incorporated herein by reference.

Generally, the synthesis of the mesoporous aluminosilicates and aluminophosphates of the present invention involves the preparation of primary and secondary zeolite building unit precursors, which are subsequently assembled to stable mesoporous zeolites in the presence of surfactant or polymeric templates. Mesoporous zeolites derived from this invention have similar acidity, thermal and hydrothermal stability as conventional zeolites, and also have high catalytic activity.

As an example, highly ordered hexagonal mesoporous aluminosilicates (MAS-5) with uniform pore sizes were synthesized from an assembly of preformed aluminosilicate precursors with cetyltrimethylammonium bromide (CTAB) surfactant. Choice of surfactant is not a limiting feature as most quaternary ammonium salts, phosphonium salts, anionic and non-ionic surfactants, and polymers which form micellar structures in solution are effective. Other examples include, but are not limited to cetyltrimethylphosphonium, octyidecyltrimethylphosphonium, cetylpyridinium, myristyltrimethylammonium, decyltrimethylammonium, dodecyltrimethylammonium, dimethyldidodecylammonium, fatty alkylamines, fatty acids, and mixtures thereof.

The aluminosilicate precursors were obtained by heating aluminosilica gels from the aqueous hydrolysis of aluminum and silicon precursors. As previously mentioned, the present invention is not limited to Al and Si precursors, and other precursors such as certain transition metal candidates can be employed. The aluminosilicate gels are heated at 80°–400° C. for 2–10 hours. The gels had a $Al_2O_3/SiO_2/TEAOH/H_2O$ molar ratio of 1.0/7.0–350/10.0–33.0/500–2000. Mesoporous MAS-5 shows extraordinary stability in both boiling water and steam. Additionally, temperature-programmed desorption of ammonia shows that the acidic strength of MAS-5 is much higher than that of conventional mesoporous materials and is comparable to that of microporous Beta zeolite. Analysis and testing of the materials of the present invention suggest that MAS-5 consists of both mesopores and micropores and that the pore walls of the MAS-5 contain primary and secondary structural building units similar to those of microporous zeolites. The unique structural features of the mesoporous aluminosilicates of the present invention are believed to be responsible for the observed strong acidity and high thermal stability of the mesoporous mesoporous aluminosilicates of well ordered hexagonal symmetry.

Additionally, the scope of the present invention is not limited to zeolites in general, or to a particular zeolite, as materials other than zeolites can be employed in the context of the present invention. Zeolites are, however, a preferred material to be employed and the use of any known or yet to be discovered zeolites in the formation of the mesoporous materials of the present invention is included within the scope of the present invention. More particularly, using precursors of other zeolite structures, one of ordinary skill in the art could readily tailor make mesoporous zeolites containing the structural features of the particular zeolite chosen. Examples of zeolites which can be employed in the context of the present invention include, but are not limited to, zeolite A, Beta zeolite, zeolite X, zeolite Y, zeolite L, zeolite ZK-5, zeolite ZK-4, zeolite ZSM-5, zeolite ZSM-11, zeolite ZSM-12, zeolite ZSM-20, ZSM-35, zeolite ZSM-23, aluminophosphates including but not limited to VPI-5 and the like, and mixtures thereof.

It is known that the aluminosilicates and/or aluminophosphates employable in the context of the present invention can be metal containing, or non-metal containing. Zeolites may contain elements such transition metals, post transition metals, Ln series and the like. Specific examples include, but are not limited to B, Ti, Ga, Zr, Ge, Va, Cr, Sb, Nb, and Y.

Good selectivity and conversion can be obtained by the process of the present invention if at least part of the isomerization is performed at a temperature of between about 100° C. and 350° C. In another embodiment, the process of the invention is performed at a temperature of between about 230° C. and 285° C. Since the conversion is also a function of the reaction/contact time, it is preferred that the fatty acid feedstock is contacted with the catalyst for a period of at least 30 minutes and reaction times of 1–16 hours are typical. An even longer period could be used if the process is operated at a lower temperature.

In general, the amount of catalyst employed in the process according to the invention is between 0.5 and 30% by weight when the process is carried out in batch or semibatch process, based on the total reaction mixture. In another embodiment the amount of catalyst used between 2.5 and 10% by weight. In still another embodiment the catalyst amounts are between 3 and 7% by weight.

When a continuous flow reactor is employed, the weight hour space velocity is between 0.01 and 100. Weight hour space velocity is defined as the weight of feed in grams passing over one gram of catalyst per hour.

Additionally, it has been found that by using the catalyst system according to this invention it is possible to reuse the catalyst. In some cases it may be desired to add fresh catalyst while optionally removing a part of the spent catalyst, and in other cases regeneration of the catalyst may be desired. Regeneration can be effected by various methods known to the skilled artisan. For example, regeneration can be accomplished by utilizing controlled oxidative regeneration and/or by washing with a solvent.

Typical feedstocks comprise fatty acids and esters derived from natural fats and oils. Such feedstocks are predominantly unsaturated linear alkylcarboxylic acids, related esters or mixtures thereof, optionally containing other organics. Since the present process is designed for isomerization or conversion of unsaturated fatty acids into branched fatty acids, it is beneficial if the fatty acid feed comprises of at least about 30% by weight of unsaturated fatty acids. In another embodiment, the feedstock comprises at least 50% by weight of unsaturated fatty acids. Any unsaturated and/or polyunsaturated fatty acid, or mixtures thereof is suitable as a feedstock in accordance with the present invention. In one embodiment, the feedstock comprises oleic acid as the unsaturated fatty acid in an amount of at least 40% by weight. In an alternative embodiment, the feedstock comprises at least 70% by weight oleic acid.

The invention also relates to the branched fatty acids and alkyl esters prepared by the processes described herein. Additionally, the invention contemplates all derivatives prepared from branched fatty acids and alkyl esters prepared by the processes described herein.

Fatty acid alkyl esters and fatty acids are versatile building blocks and conversion of these materials into a wide variety of other surfactants is possible. Some examples of the type of reactions possible are listed below. From these starting materials it is possible to produce non-ionic, anionic and cationic surfactants, all of which is within the scope of the present invention.

The branched fatty acid alkyl esters and fatty acids products of the present invention can be utilized as starting materials to prepare the same derivatives as their linear counterparts. For example, the branched alkyl esters of the present invention are readily converted into fatty acid glucamides and glycerol esters. Alkylation of polyhydridic molecules is possible. An example of this type of reaction would be reaction of a branched methyl ester with sucrose to prepare sucrose esters. Conversion of branched alkyl esters to alpha sulfonates is known. For example, branched fatty acid ester sulfonates (FAES) can be produced from branched methyl esters by sulfonation, followed by bleaching and neutralization. Branched fatty acid alkyl esters can also be converted into other branched alkyl esters by a transesterification reaction. In most cases, the smaller molecular weight alcohol is removed from the reaction mixture forcing the reaction to the desired products.

Branched fatty acids undergo many of the same reactions their linear counterparts as well as linear and branched fatty acid alkyl esters. For example, the branched fatty acid of the present invention may be converted into its' soap form by neutralization with a base. N-acyl sarcosinates can be prepared from reaction of the branched fatty acid of the present invention fatty acid or its derivatives with sarcosine. Acylated protein hydrolysates are prepared by acylation of protein hydrolysates with branched fatty acids or acid chlorides. The hydrolysates are variable in composition, depending on how they are prepared. These are mild surfactants used in often in personal care formulations. 2-Sulfoethyl esters of branched fatty acids, also known as acyl isethionates, are excellent surfactants. This family tends to be mild to the skin and hard water tolerant. Amido propyl amine and derivatives are prepared from the fatty acid or fatty acid alkyl ester. This family of surfactants has seen commercial application in laundry detergents, dishwashing liquids and many personal care formulations. Condensation of a fatty acid alkyl ester or fatty acid with an alkanolamine results in the formation of an alkanolamide. The alkanolamide and it derivatives have a variety of uses commercially depending on its specific chemical structure. Ethoxylated alkanolamides are used as compatibilizers in formulations. Many alkanolamides and derivatives are used as thickeners and foamers. Branched fatty acids can be alkoxylated with ethylene oxide, propylene oxide and butylenes oxide to make a useful family of non-ionic surfactants. Branched fatty acids can be converted into nitriles which are the building blocks for a large variety of cationic and amine surfactants. Branched fatty acids acan also be used in a reaction to prepare esteramines which are quaternized, esterquats. The major use of esterquats is in household fabric softeners.

Conversion of the branched alkyl esters and branched fatty acids into branched alcohols can also be done. The alcohol is another building block to prepare other types of surfactants. Alcohols are used to prepare alkyl polyglycosides (APGs). These materials offer a hydrophile based on a natural sugar. Conversion of the alcohol into amines and quaternaries occurs readily and is a commercially important reaction in the preparation of cationic surfactants. Non-ionic surfactants are prepared by alkoxylation of alcohols. Common alkoxylation agents are ethylene oxide, propylene oxide and butylene oxide. Conversion of alcohols (with or without alkoxylation) to alcohol sulfates is a commercially important process. The use of alcohol sulfates in laundry is increasing especially in Europe. Other areas of use include shampoos, textile processing and emulsion polymerization. Alcohols can also be converted in phosphate esters. Both mono and di phosphate esters can be favored depending on the reaction conditions. Polyalkoxycarbonates are produced by the reaction of sodium chloroacetate with an alcohol ethoxylate, or from acrylic acid and an alcohol ethoxylate. These can also be made by direct oxidation of the alcohol ethoxylate under carefully controlled conditions.

The aforementioned description is merely illustrative and not intended to limit the scope of the invention. Accordingly, one of ordinary skill in the art would readily recognize that the branched products of the present invention, like their linear counterparts, can be readily employed as starting materials in the preparation of numerous derivatives as illustrated by the following chart. Any and all of the derivatives prepared from the novel products of the present invention are within the scope of the present invention.

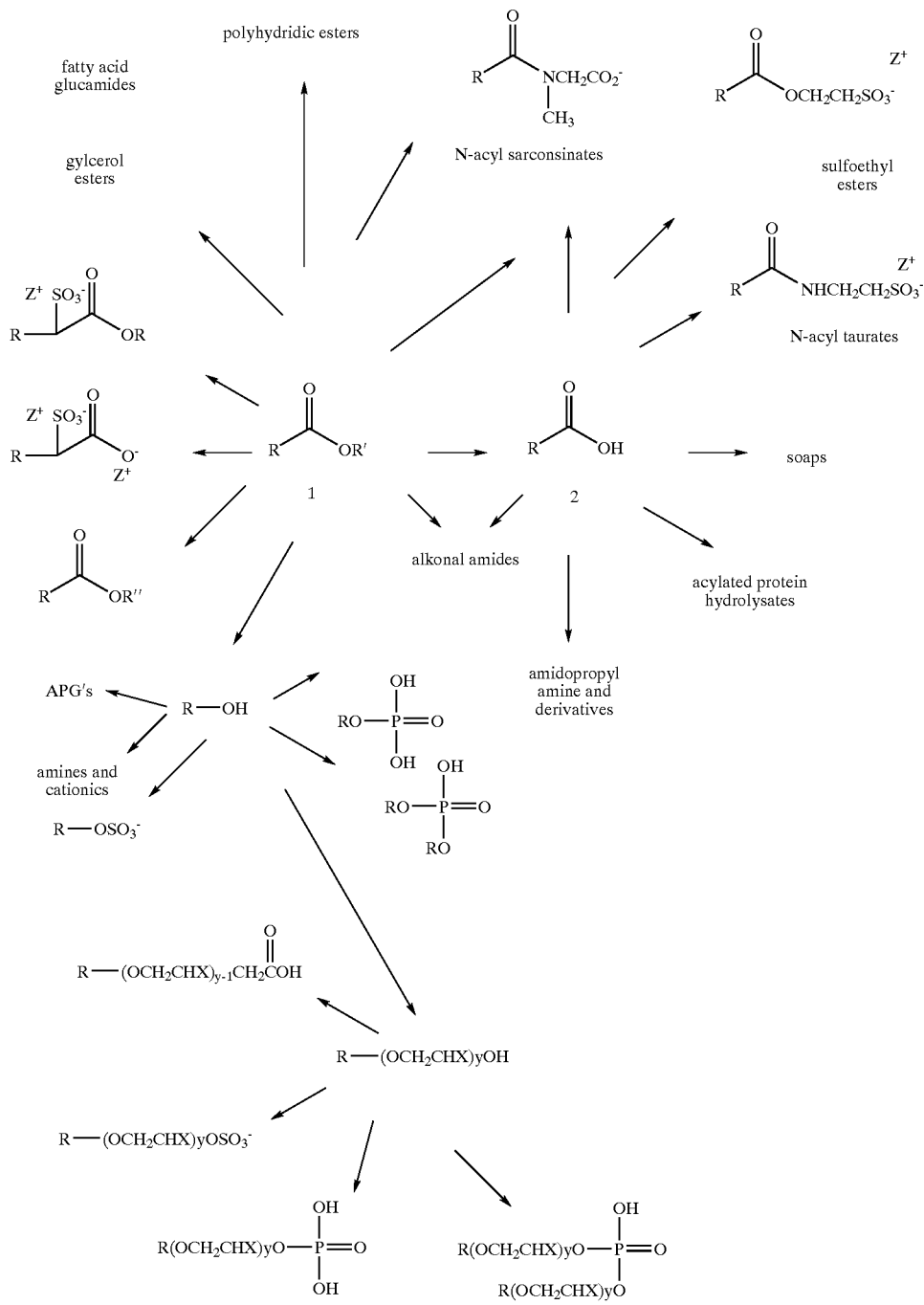

The invention will now be illustrated by the following non-limiting examples.

Synthesis of Strongly Acidic and Hydrothermally Stable MAS-5 Containing Beta Zeolite Building Units A highly ordered hexagonal mesoporous aluminosilicate was synthesized in this laboratory following a procedure similar to that described in Xiao et al's paper (*J. Am. Chem. Soc.*, 2001, 123, 5014–5021). A proton form MAS-5($H^+$-MAS-5) was prepared by ion exchange of $Na^+$ for $NH_4^+$ from the $Na^+$-MAS-5 mesoporous zeolite, followed by drying and a calcination in air at 500° C. for 2 h. This $H^+$-MAS-5 sample has a sharp pore size distribution at ~37 Å with zeolite beta wall structure at Si/Al (mole ratio) of 25.

Table 1 shows some physical properties of the $Na^+$-MAS-5 sample.

TABLE 1

Physical properties of $Na^+$-MAS-5 sample

| Sample # | BET SA (m²/g) | Pore Area (m²/g) | Pore Volume (cc/g) | Average Pore Diameter Å |
|---|---|---|---|---|
| 1798-92 | 907 | 1336 | 1.25 | 37 |

The reaction result of the $H^+$-MAS-5 sample for oleic acid isomerization was presented in the examples below.

EXAMPLE 1

Oleic Acid Isomerization on Mesoporous Aluminosilicate (MAS-5)

2 g of $H^+$-MAS-5 (SAR 25) and 20 g of oleic acid were loaded into a 135 ml autoclave reactor. After sealed, the reactor was purged three times with nitrogen. A nitrogen pressure of 50 psig was approached at room temperature. With an active stir at 1000 RPM, the mixture of oleic acid and catalyst was heated up to 250° C. within 30 minutes and maintained for 5 h. After cooled down to room temperature within 20 minutes, the mixture was taken out of the reactor. The product was separated from the solid catalyst by filtration with slightly heating and analyzed with a GC. Compositions of oleic acid and reaction product (sample 1) appear in Table 2. The calculated $C_{18}^1$ conversion and branched $C_{18}^1$(i-$C_{18}$) selectivity are tabulated in Table 3.

EXAMPLE 2

The used catalyst from Example 1 was washed with 200 ml of acetone and then dried at 100° C. overnight. It was mixed with 18 g of oleic acid and loaded to the reactor. After 5 h reaction under the same conditions as in Example 1, the product (sample 2) was analyzed by GC. Table 2 and 3 show the results.

TABLE 3

$C_{18}^1$ conversion

| Example | $C_{18}^1$ conversion wt % |
|---|---|
| 1 | 60 |
| 2 | 44 |

COMPARATIVE EXAMPLE

Table 4 shows the result of a of a Hbeta (sar 25, extrudates) zeolite for oleic acid isomerization under the same conditions described above.

TABLE 4

$C_{18}^1$ conversion and branched $C_{18}^1$ selectivity

| catalyst | $C_{18}^1$ conversion wt % |
|---|---|
| HBeta (SAR 25) | 49 |

We claim:

1. A process for the isomerization of a feedstock which comprises unsaturated linear fatty acids, alkyl esters of unsaturated fatty acids or mixtures thereof, wherein said process comprises subjecting said feedstock to an isomerization reaction in the presence of an acidic catalyst, wherein said acidic catalyst comprises a mesoporous crystalline phase having pore walls containing primary and secondary crystalline building unit structures.

2. The process of claim 1 wherein said catalyst comprises both mesopores and micropores.

3. The process of claim 2 wherein said catalyst is a mesoporous aluminosilicate or a mesoporous metal containing aluminosilicate.

4. The process of claim 3 wherein said mesoporous aluminosilicate is a mesoporous zeolite.

5. The process of claim 4 wherein said mesoporous zeolite catalyst material comprises mesopores of 15–500 Å and primary and secondary nanosized zeolite structural units in the walls that separate mesopores.

6. The process of claim 1, wherein the isomerization of said feedstock comprises branching of the fatty acids or alkyl esters thereof.

7. The process of claim 6 wherein said mesoporous zeolite comprises hexagonal mesopores, the pore wall structures of said mesopores containing primary and secondary zeolite building units.

8. The process of claim 5 wherein said mesoporous zeolite is characterized by an IR absorption at 400–600 $cm^{-1}$.

TABLE 2

Oleic acid isomerization on $H^+$-MAS-5 and branched $C_{18}^1$ selectivity

| Sample | <=$C_1$ | i-$C_{12}$ | $C_{12}$ | i-$C_{14}$ | $C_{14}^1$ | $C_{14}$ | i-$C_{16}$ | $C_{16}^1$ | $C_{16}$ | i-$C_{18}$ | $C_{18}^1$ | $C_{18}$ | lactone | >$C_{18}$ |
|---|---|---|---|---|---|---|---|---|---|---|---|---|---|---|
| Feed | 0 | 0.15 | 0.08 | 0.63 | 0.48 | 1.92 | 0.74 | 4.99 | 4.07 | 1.95 | 79.58 | 1.92 | 3.49 | — |
| 1 | 0.25 | 0.44 | 0.24 | 1.74 | 0 | 2.43 | 3.09 | 1.77 | 6.71 | 31.12 | 32.03 | 3.99 | 15.85 | 0.34 |
| 2 | 0.07 | 0.34 | 1.11 | 0 | 0 | 2.09 | 2.18 | 2.27 | 5.86 | 21.39 | 45.01 | 2.67 | 16.55 | 0.46 |

9. The process of claim 1 wherein said primary and or secondary crystalline building units are based on at least one zeolite selected from the group consisting of zeolite A, Beta zeolite, zeolite X, zeolite Y, zeolite L, zeolite ZK-5, zeolite ZK-4, zeolite ZSM-5, zeolite ZSM-11, zeolite ZSM-12, zeolite ZSM-20, ZSM-35, zeolite ZSM-23, VPI-5 and mixtures thereof.

10. The process according to claim 1 wherein the feedstock comprises of at least 50% by weight of unsaturated fatty acids, alkyl esters of unsaturated fatty acids or mixtures thereof.

11. The process of claim 10 wherein the feedstock comprises of at least 70% by weight oleic acid.

12. The process claim 1 wherein at least part of the isomerization is performed at a temperature of between 100° C. and 350° C.

13. The process of claim 12 wherein at least part of the isomerization is carried out at a temperature of between 230° C. and 285° C.

14. The process of claim 1 wherein said isomerization is conducted in a batch reactor.

15. The process of claim 1 wherein said isomerization is conducted in a fixed bed continuous flow reactor.

16. The process of claim 1 wherein the feedstock is contacted with the catalyst for a period of at least 30 minutes.

17. The process of claim 14 wherein the amount of catalyst used is between 0.5 and 30% by weight of the feedstock in the batch reactor.

18. The process of claim 15 wherein the weight hour space velocity is between 0.01 and 100 in a continuous flow reactor.

19. A process for the isomerization of a feedstock which comprises unsaturated linear fatty acids, alkyl esters of unsaturated fatty acids or mixtures thereof, wherein said process comprises subjecting said feedstock to an isomerization reaction in the presence of an acidic catalyst, wherein said acidic catalyst comprises a aluminophosphate or a metal containing aluminophosphate.

20. The process of claim 19 wherein said catalyst comprises a mesoporous crystalline phase having pore walls containing primary and secondary crystalline building unit structures comprising aluminophosphate or a metal containing aluminophosphate.

21. A branched fatty acid or alkyl ester thereof prepared by isomerizing a feedstock which comprises unsaturated linear fatty acids, alkyl esters of unsaturated fatty acids or mixtures thereof, wherein said process comprises subjecting said feedstock to an isomerization reaction in the presence of an acidic catalyst, wherein said acidic catalyst comprises a mesoporous crystalline phase having pore walls containing primary and secondary crystalline building unit structures.

22. The branched fatty acid or alkyl ester thereof of claim 21 wherein said catalyst comprises both mesopores and micropores.

23. The branched fatty acid or alkyl ester thereof of claim 22 wherein said catalyst is a mesoporous aluminosilicate or a mesoporous metal containing aluminosilicate.

24. The branched fatty acid or alkyl ester thereof of claim 23 wherein said mesoporous aluminosilicate is a mesoporous zeolite.

25. The branched fatty acid or alkyl ester thereof of claim 24 wherein said mesoporous zeolite catalyst material comprises mesopores of 15–500 Å and primary and secondary nanosized zeolite structural units in the walls that separate mesopores.

26. The branched fatty acid or alkyl ester thereof of claim 25 wherein said mesoporous zeolite comprises hexagonal mesopores, the pore wall structures of said mesopores containing primary and secondary zeolite building units.

27. The branched fatty acid or alkyl ester thereof of claim 21 wherein said mesoporous zeolite is characterized by an IR absorption at 400–600 $cm^{-1}$.

28. The branched fatty acid or alkyl ester thereof of claim 21 wherein said primary and or secondary crystalline building units are based on at least one zeolite selected from the group consisting of zeolite A, Beta zeolite, zeolite X, zeolite Y, zeolite L, zeolite ZK-5, zeolite ZK-4, zeolite ZSM-5, zeolite ZSM-11, zeolite ZSM-12, zeolite ZSM-20, ZSM-35, zeolite ZSM-23, VPI-5 and mixtures thereof.

29. The branched fatty acid or alkyl ester thereof according to claim 21 wherein the feedstock comprises of at least 50% by weight of unsaturated fatty acids, alkyl esters of unsaturated fatty acids or mixtures thereof.

30. The branched fatty acid or alkyl ester thereof of claim 21 wherein at least part of the isomerization is performed at a temperature of between 100° C. and 350° C.

31. The process of claim 30 wherein the amount of catalyst used is between 0.5 and 30% by weight of the feedstock.

32. A derivative prepared from the branched fatty acid or alkyl ester thereof of claim 21 wherein said derivative is selected from the group consisting essentially of amphoteric, non-ionic, anionic and cationic surfactants.

33. The derivative of claim 32 wherein said derivative is selected from the group consisting essentially of fatty acid glucamides, glycerol esters, polyhydric esters, sulfoesters, sucrose esters, alpha sulfonates, N-acyl sarcosinates, acylated protein hydrolysates, acyl isethionates, amido propyl amine and derivatives thereof, alkanolamide, ethoxylated alkanolamides, nitrites, N-aryl taurates, soaps, esteramines, esterquats, alkyl polyglycosides (APGs), alcohol sulfates, phosphate esters, polyalkoxycarbonates and mixtures thereof.

* * * * *